United States Patent [19]

Siegel

[11] 4,415,668
[45] Nov. 15, 1983

[54] CELL CULTURE

[75] Inventor: Don L. Siegel, Brookline, Mass.

[73] Assignee: President and Fellows of Harvard College, Cambridge, Mass.

[21] Appl. No.: 255,480

[22] Filed: Apr. 20, 1981

[51] Int. Cl.³ .................. C12N 5/02; C12N 11/08; C12M 3/02

[52] U.S. Cl. .................................. 435/241; 435/286; 435/180

[58] Field of Search ............... 435/2, 240, 241, 284, 435/286, 178, 180

[56] References Cited

U.S. PATENT DOCUMENTS 4,036,693  7/1977  Levine et al. ................. 435/240
4,189,534  2/1980  Levine et al. ................. 435/240

OTHER PUBLICATIONS

Jost et al. "The Mode of Adsorption of Proteins to Aliphatic and Aromatic Amines Coupled to Cyanogen Bromide-Activated Agarose" Biochemica et Biophysica Acta, 362 (1974) pp. 75–82.

Spurr, "A Low-Viscosity Epoxy Resin Embedding Medium for Electron Microscopy" Journal of Ultrastructure Research 26 (1969) pp. 31–43.

Sargent et al, "The Use of Polystyrene Microcarriers to prepare Cell Monolayers for Transmission Electron Microscopy", Journal of Microscopy, vol. 122(2) (5-1981) pp. 209–212.

Primary Examiner—Thomas G. Wiseman
Assistant Examiner—John Tarcza

[57] ABSTRACT

Improved cell culture microcarriers having controlled amphipathic (hydrophobic and polar) properties and controlled positive charge capacities, which make these microcarriers controllable in size in aqueous or non-aqueous environments and which produce outstanding growth of anchorage-dependent cells, and methods for their use.

6 Claims, No Drawings

CELL CULTURE

BACKGROUND OF THE INVENTION

The government has rights to this invention pursuant to NIH Grant No. GM-20396.

This invention relates to cell culture microcarriers in the field of cell biology.

The ability to grow mammalian cells and carefully study their growth is important in the laboratory and in industry. Large-scale growth of anchorage-independent cells (suspension cultures) has been achieved by applying the techniques of submerged cultivation of microbial cells. Other cell types have not been adapted for growth in suspension culture to date, and will grow only if they can become attached to an appropriate surface (anchorage-dependent cells).

Considerable progress has been made in recent years on large-scale propagation of anchorage-dependent cells; of many alternatives proposed, the microcarrier systems appear to offer the most advantages. Microcarrier systems involving the use of diethylaminoethyl (DEAE)—substituted dextran beads have been proposed but have produced certain deleterious effects among which are high initial cell death rate and inadequate cell growth for those cells which attach to the microcarriers.

One solution to overcoming some of the deleterious effects is described in U.S. Pat. No. 4,036,693, issued on July 19, 1977 to Levine et al. Therein, a method for treating these commercially available ion exchange resins with macromolecular polyanions, such as carboxymethylcellulose, is proposed. While this method has proven successful, it would clearly be more advantageous if the beads could be manufactured initially to have properties designed for outstanding growth of anchorage-dependent cells. It has also been proposed in Levine et al. U.S. Pat. No. 4,189,534 to control the charge capacity of microcarriers within a certain range to promote growth of anchorage-dependent cell types.

The advantages of such microcarriers include the ability to obtain great increases in the ratio of growth surface area to vessel volume, the use of a single homogeneous reaction vessel, a batch or semi-batch operation, the ability to maintain control of conditions with simple feedback methods, and a reduction in the number of steps required. Also, having a homogeneous mixture of microcarriers makes it possible to take a representative sample of a culture at any time during cell growth for biochemical analysis and/or observation. However, the character of such microcarriers allows observation only by conventional light microscopy using stains soluble in aqueous media. The reason for this is that the existing microcarriers shrink on exposure to organic media used for certain stains and for electron microscopy, causing a distorted convoluted surface on the microcarrier and resultant damage to the attached cells.

SUMMARY OF THE INVENTION

It has now been discovered that microcarriers which are "amphipathic", having both hydrophobic groups and polar groups (such as hydroxyl), do not change in size when transferred from a hydrophilic aqueous cell growth medium to a hydrophobic organic environment. This property allows these microcarriers to be closely studied through use of electron microscopy and conventional light microscopy where it is desirable to use stains soluble only in organic media.

Microcarrier beads have been produced with hydrophobic and polar properties and controlled positive charge according to this invention and such beads have been used to obtain cell growth equal to growth on beads disclosed in the prior art.

The microcarrier of this invention can be synthesized from a polymeric base material which is treated to obtain polar properties, such as cross-linked dextran beads containing hydroxyl groups. These beads are then treated to obtain hydrophobic properties, such as by hydroxy propylating the hydroxy containing cross-linked dextran with 1,2-epoxypropane. To obtain a positive charge, the beads are then treated with a tertiary or quaternary amine, such as diethylaminoethylchloride or its hydrochloride salt. The hydrophobicity, polarity (hydrophilicity) and positive charge can be controlled by adjusting the initial concentration of the reactants and the time and temperature of the reaction.

Microcarriers of this invention can be used in cell cultures with all the advantages of prior microcarriers and the added advantage of hydrophobicity which allows exposure of the beads to organic solvents without deleterious effects and which may enhance the growth of certain cells which thrive in a partially hydrophobic environment.

DESCRIPTION OF THE PREFERRED EMBODIMENTS

The microcarriers of this invention are small, discrete particles suitable for cell attachment and growth made from a suitable polymeric support material. The microcarriers are often, but not necessarily, porous beads on the outer surfaces of which cells attach and grow. They are amphipathic (i.e. having both hydrophobic and polar (hydrophilic) properties) and also have positive charge properties. It is the addition of the hydrophobic property which causes the improvements which are inherent in these microcarriers.

The microcarriers that are presently available, and commonly used, shrink to a fraction of their original surface area when exposed to organic solvents, e.g. approximately 25% of their original surface area when exposed to ethanol in preparation for electron microscopy. This shrinking destroys the normal cell shape and the cell-microcarrier interface. The distortions, convolutions and artifacts which are created make meaningful analysis by electron microscopy impossible.

The microcarriers of the present invention, essentially do not shrink when transferred from a hydrophilic aqueous cell-growth medium to a hydrophobic organic environment such as that required for electron microscopy. This makes them particularly useful for large scale industrial production of cells since accurate monitoring of cell adhesion and growth is possible. The additional analytical techniques available due to this improvement are also beneficial in studying the surface of the microcarriers for damage (e.g. for "pockmarks" and cavities caused by non-optimum agitation) and for cell-microcarrier surface interactions.

The microcarriers of this invention may be prepared by starting with a suitable polymeric material such as a high molecular weight polymer containing reactive groups such as hydroxyls or amides. Examples include: polysaccharides such as dextran, dextrin, starch, or cellulose; polyvinyl alcohol; and, hydroxy-substituted acrylate or methacrylate polymers; all of which contain reactive hydroxyl groups. Other examples include polyacrylamide which contains reactive amide groups. The preferred polymeric material is cross-linked dextran, available commercially as Sephadex ®. The preferred cross-linked dextran is cross-linked such that there are, on the average, two to four hydroxyl groups per monomer unit.

Hydrophobic chemical groups are added to the polymeric material by reaction with the reactive groups listed above. The degree of hydrophobicity of the microcarrier is determined by the hydrophobicity of the attached ligand and the number of them attached per monomer unit. For example, with the preferred dextran each monomer contains, on the average, three reactive hydroxyl groups (neglecting cross-linked points) which can be reacted. Among the reagents which can be employed to introduce the desired hydrophobic groups are ethylene oxide, propylene oxide, other alkylene oxides having up to twenty-one carbon atoms, and the like, which serve to introduce such hydrophobic groups as hydroxyethyl, hydroxypropyl, hydroxyalkoxypropyl in which each alkoxy contains up to eighteen carbon atoms, and the like. The preferred hydrophobic group is hydroxypropyl and the preferred alkylene oxide has up to six carbon atoms which serves to introduce hydroxyalkoxypropyl groups in which each alkoxy contains up to three carbon atoms. Hydroxypropyl dextran can be made by treating dextran with an aqueous alkaline material (such as sodium hydroxide) and then treating with propylene oxide (1,2-epoxypropane). The degree of substitution (hydrophobicity) may be controlled by adjusting the amount of 1,2-epoxypropane or by adjusting the alkalinity, (e.g. by using sodium carbonate).

Hydroxypropyl dextran can be purchased commercially as Sephadex ® LH-60, a material which is fully hydroxypropylated, i.e. having approximately three hydroxypropyl groups per glucose monomer unit. Each hydroxypropyl group is available for further reaction by introduction of charged or uncharged ligands such as DEAE, carboxyls, hydrocarbons, etc.

A positive charge is then given to the hydrophobic polymer by treating with amino groups in an alkaline environment, as described for example in U.S. Pat. No. 4,189,534 issued on Feb. 19, 1980 to Levine et al, the disclosure of which is incorporated herein by reference. Either tertiary or quaternary amines are suitable sources of positively charged groups which can be reacted with the hydroxy-containing polymers. Particularly preferred materials are chloro- or bromo-substituted tertiary amines or salts thereof, such as diethylaminoethylchloride, diethylaminoethylbromide, dimethylaminoethylchloride, dimethylaminoethylbromide, diethylaminomethylchloride, diethylaminomethylbromide, di-(hydroxyethyl)-aminoethylchloride, di-(hydroxyethyl)-aminoethylbromide, di-(hydroxyethyl)-aminomethylchloride, di-(hydroxyethyl)aminomethylbromide, β-morpholinoethylethylchloride, β-morpholinoethylbromide, β-morpholinomethylchloride, β-morpholinomethylbromide and salts thereof, for example, the hydrochlorides.

Stains used in many organic solvents would be compatible with the amphipathic, positively charged microcarriers of this invention. Examples include orange G and fast green which are routinely used with crystal violet and are ideal for visualizing cytoplasmic and nuclear structures as described by Johansen, DA, *Plant Microtechniques*, McGraw-Hill, Inc., New York, 1940. Amphipathic microcarriers should also be stable with a range of non-aqueous solvents used for adjusting the refractive index. Examples include dioxane, xylene, and oils. Amphipathic microcarriers should also be stable with various mounting media such as balsam, styrax, corn syrup, Spurr's resin, (Spurr, J. Ultrastructure Research, Vol. 26, 31-43 (1969)) and the like.

This invention is further illustrated by the following examples.

EXAMPLE 1

Preparation of Improved Microcarriers

Dry, uncharged, crosslinked, amphipathic dextran beads are sieved to obtain those of approximately 75 μm in diameter. One gram of this fraction is added to 63 ml of distilled water and the beads are allowed to swell at room temperature. An adequate commercial source of dry, hydroxypropylated dextran is Sephadex ® LH-60 from Pharmacia Fine Chemicals, Piscataway, N.J. The swollen beads are then cooled to 4° C. and a sodium hydroxide solution (22.3 g in 31.5 ml distilled water) is added dropwise to the rapidly stirring bead suspension. After 30′, diethylaminoethylchloride:chloride (19.6 g in 25.4 ml distilled water) is added slowly and the mixture is agitated vigorously in a shaking water bath for one hour at 80°. The beads are then separated from the reaction mixture by filtration through a sintered glass funnel and washed with ethanol, water, 10% ammonium hydroxide, ethanol, 0.1 N HCl, 0.001 N HCl, ethanol and water.

Beads made by this procedure contain 1.6 to 1.8 meq of charge capacity per gram of dry hydroxypropylated crosslinked dextran which is equivalent to 3.2 to 3.6 meq of charge capacity per gram of dry hydrophilic crosslinked dextran (assuming three hydroxypropyl groups per glucose monomer). This charge capacity can be characterized by measuring the anion exchange capacity of the beads as follows. The bead preparations are washed thoroughly with 0.1 N HCl to saturate all exchange sites with $Cl^-$ ions. They are then rinsed with $10^{-4}$ N HCl to remove unbound chloride ions. Subsequently, the beads are washed with a 10% (w/w) sodium sulfate solution to countersaturate the exchange sites with $SO_4^{-2}$. The effluent of the sodium sulfate wash is collected and contains liberated chloride ions. This solution is titrated with 0.1 M silver nitrate using dilute potassium chromate as an indicator.

After titration, the beads are washed thoroughly with distilled water and phosphate-buffered saline, and autoclaved. This procedure yields hydrated beads of approximately 120–200 μm in diameter, which carry 1.6 to 1.8 meq of charge capacity per gram of dry, untreated, hydroxypropylated, crosslinked dextran.

EXAMPLE 2

Cell Growth

Rat embryo fibroblasts infected with the B77 temperature-sensitive strain of Rous sarcoma virus were maintained in plastic roller bottles in Dulbecco's Modified Eagle's medium (Flow Laboratories, McLean, Va.) supplemented with 2 mM glutamine, 100 units/ml penicillin, and 10% fetal calf serum (Difco Laboratories, Detroit, Mich.) An average doubling time of 23 h was observed under these conditions.

Microcarrier cultures were initiated by combining 100 ml growth medium, $2.5 \times 10^7$ cells, and 0.25 g of microcarriers in a 250-ml glass spinner bottle (6.5 cm in diameter) equipped with a 4.5-cm magnetically driven Teflon coated stir bar. Stirring speed was approximately 90 rpm.

Experiments were conducted as above with the dextran base, positively charged microcarriers described in Levine U.S. Pat. No. 4,189,534 and with the microcarriers of this invention described in Example 1. The relative amounts of microcarriers used were adjusted to give equal amounts of surface area (approximately 1400 cm$^2$/100 ml spinner culture). Cultures were sampled directly and enumerated by counted nuclei using the modification of the method of Sanford et al. (Sanford, K. K., Earle, W. R., Evans, V. J., Waltz, H. K. and Shannon, J. E. (1951) J. Natl. Cancer Inst., Vol. 11, 773) as described by van Wezel (van Wezel, A. L. (1973). *Tissue Culture, Methods and Application*. Kruse, P. F. and Patterson, M. R. (eds.), pp. 372–377, Academic Press, New York).

The rate of increase of cell concentration was essentially the same each microcarrier.

EXAMPLE 3

Preparation for Electron Microscopy

All fixations were performed in at least 10 volumes of fixative and all washes utilized at least 3×10 volumes of buffer at room temperature in 4 ml screw-capped vials. During each step, the carriers were kept in suspension by constant rotation on a rotator and removal of incubation media was accomplished by allowing the beads to settle at 1×g for several minutes. Fixatives, embedding medium, and capsules were from Polysciences, Inc., Warrington, Pa.

Plain beads or cell-covered beads were washed with phosphate-buffered saline (PBS) and then fixed with 3% glutaraldehyde in PBS, pH 7.4, for one hour. They were washed with PBS to remove glutaraldehyde and then with veronal-acetate buffer containing 2.4 mM CaCl$_2$ and 60 mM NaCl, pH 7.4. The preparation was post-fixed with 1% OsO$_4$ for 2 h in this buffer, washed with veronal-acetate/NaCl buffer without calcium, and washed with veronal-acetate/NaCl buffer, pH 5.5. En bloc staining was performed with 0.5% uranyl acetate in this buffer for 2 h. After washing the stain away, the bead suspension was dehydrated in ethanol/veronal-acetate/NaCl buffer mixtures according to the following schedule: 10% ethanol, 15'; 30% ethanol, 15'; 50% ethanol, 15'; 70% ethanol, 15 hours; 90% ethanol, 30'; and 3×100% ethanol for 1 h each. They were then embedded in Spurr low-viscosity embedding medium according to the following resin/ethanol ratios and schedule: 1:3, 1 h; 1:1, 1 h; 3:1, 1 h; 100% resin, 1 h; and 100% resin, 12 h. The samples were then placed in embedding capsules and hardened for 18 h at 70°. Silver sections of the blocks were cut with a Reichert Om U2 Ultramicrotome, picked up onto 200-mesh grids, stained with 2% uranyl acetate and lead citrate (Reynolds, E., (1963) *J. Cell Biol.*, 17, 208) and examined in a Phillips 301 Electron Microscope at 60 kV.

Experiments were conducted to measure the shrinkage of the following microcarriers: A positively by charged dextran base microcarrier, such as described in Levine U.S. Pat. No. 4,189,534; an polyacrylamide base microcarrier commercially available as "Bio-Rad Biocarriers"; and, the microcarrier of this invention as described in Example 1. Bare beads were prepared for electron microscopy as above, and the diameters of 200 beads at each step were measured using a conventional light microscope.

These experiments showed that microcarriers of this invention remained at essentially the same size at all stages of preparation. Conventional positively charged, dextran base, microcarriers, (as described in U.S. Pat. No. 4,189,534) started to exhibit shrinking at the 70% ethanol level and by completion of the dehydration were only 50% of their original diameter (25% original surface area). Similar shrinking was observed in conventional polyacrylamide base microcarriers.

What is claimed is:

1. The method of growing anchorage-dependent cells in microcarrier cell culture and preparation for examination in a non-aqueous organic solvent environment comprising growing cells in aqueous environment on microcarriers comprising polymeric support material having reactive chemical moieties thereon selected from the group consisting of hydroxyl and amide moieties and having bonded thereto hydrophobic chemical moieties selected from the group consisting of hydroxyethyl, hydroxypropyl and hydroxyalkoxypropyl moieties and bonded thereto an amount of positively charged chemical moieties to provide an exchange capacity within the range of between about 0.1 and about 4.5 meq/gram of dry untreated polymeric support material, staining and transferring said microcarriers bearing said cells from said aqueous cell growth environment to a non-aqueous organic solvent environment without shrinkage of said microcarriers, and examining the unshrunk microcarriers bearing said cells previously subjected to staining.

2. The method of claim 1, wherein said polymeric support material comprises a cross-linked polysaccharide having reactive hydroxyl moieties thereon.

3. The method of claim 2, wherein said hydrophobic chemical moieties comprise hydroxypropyl moieties.

4. The method of claim 2, wherein all of said reactive hydroxyl moieties have bonded thereto a hydroxypropyl moiety.

5. The method of claim 3, wherein said polysaccharide comprises cross-linked dextran.

6. The method of claim 2, wherein said positively charged chemical moieties comprise teritary or quaternary amine moieties.

* * * * *